(12) United States Patent
Shimizu et al.

(10) Patent No.: US 8,142,635 B2
(45) Date of Patent: Mar. 27, 2012

(54) CAPILLARY ARRAY

(75) Inventors: Yasushi Shimizu, Hitachinaka (JP);
Toshiaki Kita, Hitachinaka (JP);
Kiyoshi Tsukada, Mito (JP); Akihiro Suzuki, Hitachinaka (JP); Tomonari Morioka, Hitachinaka (JP); Masaya Kojima, Mito (JP); Ryoji Inaba, Hitachinaka (JP); Daizo Tokinaga, Hachioji (JP); Shuhei Yamamoto, Hitachinaka (JP); Yoshiyuki Okishima, Minori (JP); Masao Fukunaga, Itabashi (JP); Takayasu Furukawa, Hitachinaka (JP); Tomohiro Shoji, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/843,103

(22) Filed: Jul. 26, 2010

(65) Prior Publication Data

US 2010/0288642 A1   Nov. 18, 2010

Related U.S. Application Data

(63) Continuation of application No. 11/300,377, filed on Dec. 15, 2005, now Pat. No. 7,785,458, which is a continuation of application No. 09/845,303, filed on May 1, 2001, now Pat. No. 7,005,052.

(30) Foreign Application Priority Data

May 15, 2000 (JP) .................................. 2000-147497

(51) Int. Cl.
*C02F 1/40* (2006.01)

(52) U.S. Cl. .......... 204/600; 204/601; 204/603; 204/604

(58) Field of Classification Search ................. 204/601, 204/603, 600, 452; 250/458
See application file for complete search history.

(56) References Cited

U.S. PATENT DOCUMENTS

| 5,274,240 A | 12/1993 | Mathies et al. |
| 5,366,608 A | 11/1994 | Kambara |
| 5,439,578 A | 8/1995 | Dovichi et al. |
| 5,516,409 A | 5/1996 | Kambara |
| 5,529,679 A | 6/1996 | Takahashi et al. |
| 5,582,705 A | 12/1996 | Yeung et al. |
| 5,730,850 A * | 3/1998 | Kambara et al. ............. 204/603 |
| 5,790,727 A | 8/1998 | Dhadawal et al. |

FOREIGN PATENT DOCUMENTS

JP   9-96623   4/1997

* cited by examiner

*Primary Examiner* — Ling Choi
*Assistant Examiner* — Monique Peets
(74) *Attorney, Agent, or Firm* — Dickstein Shapiro LLP

(57) ABSTRACT

A capillary array includes a light detection portion, a sample supply portion, a buffer solution supply portion and a voltage application portion which are necessary functions for electrophoresis, thereby, when assembling the capillary array into an electrophoresis apparatus, the same can be immediately used. Accordingly, a capillary array is provided which can be easily incorporated into an electrophoresis apparatus.

2 Claims, 6 Drawing Sheets

CAPILLARY ARRAY

This is a continuation of application Ser. No. 11/300,377, filed Dec. 15, 2005, now U.S. Pat. No. 7,785,458 which is a continuation of application Ser. No. 09/845,303, filed May 1, 2001, now U.S. Pat. No. 7,005,052, issued Feb. 28, 2006, which are hereby incorporated by reference in their entireties.

BACKGROUND OF THE INVENTION

1. Field of the Invention

The present invention relates to a capillary array used for a capillary array electrophoresis apparatus which separates and analyzes samples such as DNA and protein.

2. Conventional Art

An application technology in which an array is constituted by combining a plurality of capillaries, an electrophoresis medium and a sample to be separated and analyzed are supplied to the respective capillaries and moved therethrough to thereby separate and analyze the object sample is well known, wherein a sample such as DNA and protein labelled by a fluorescent material is supplied to the capillaries. Such application technology is, for example, disclosed in U.S. Pat. Nos. 5,366,608, 5,529,679, 5,516,409, 5,730,850, 5,790,727, 5,582,705, 5,439,578 and 5,274,240. In view of a through-put of the separation and analysis, it is much more advantageous to use electrophoresis with multi capillaries rather than electrophoresis with a flat plate gel.

JP-A-9-96623 (1997) discloses an application technology which separates and analyzes a fluorescent labelled sample through electrophoresis by making use of a multi-capillaries.

A capillary array electrophoresis apparatus is basically constituted by such as a capillary array, an excitation light system including a laser beam source, a light receiving optical system which detects fluorescence and a voltage application unit which causes electrophoresis. In such capillary array electrophoresis apparatus the capillary array is constituted by aligning a plurality of capillaries in a plane shape, and a laser beam is irradiated to the capillaries which are filled by a sample (fluorescent sample) labelled by a fluorescent material in parallel direction with the capillary aligning direction, then, through the lens action of the capillaries the laser beam is condensed and the laser beam is irradiated to the fluorescent sample in all of the capillaries when the laser beam is irradiated, the fluorescent sample emits fluorescence. Through detection by the light receiving optical system of the fluorescence emitted from the fluorescent sample in a direction substantially perpendicular to the laser beam irradiation direction, the measurement of the sample is performed.

The above patent document discloses a schematic diagram of a detection portion for the array, but does not disclose an entire structure of a specific capillary array for assembling the same into the electrophoresis apparatus.

SUMMARY OF THE INVENTION

An object of the present invention is to provide a capillary array having a specific structure which is suitable for a capillary array electrophoresis.

The present invention is to provide a capillary array which comprises a light detection portion, a buffer solution injection portion and an electrode built-in capillary head. The capillary array of the present invention is provided with functions necessary for an electrophoresis apparatus.

More specifically, the present invention provides a capillary array which comprises a plurality of capillaries which includes a polymer protective film on the surface thereof and of which one ends are bundled and of which other ends are spread; a light detection portion in which the capillaries are juxtaposed each other and are aligned substantially on a plane and the polymer protective films therein are removed; a head which holds the spread capillaries integrally, an electrode which is built-in in the head, electrically connected to the head and is immersed in a sample solution; and another electrode provided at the bundled capillaries.

Another embodiment of the present invention provides a capillary array in which one ends of a plurality of capillaries with a protective coat are bundled and the end portion thereof are aligned in flat so as to form a buffer solution injection port; the other ends of the capillaries penetrate through a capillary head with a built-in electrode and are inserted into metal tubes which are connected electrically to the built-in electrode, a light detection portion is formed at an intermediate portion of the capillary array wherein the protective coat of the capillaries is removed, the protective coat removed capillaries are sandwiched between first and second support substrates, a window which permits emission of fluorescence is formed on one of the first and second support substrates and a black coating is formed on the other of the first and second support substrates at a position corresponding to the fluorescence emission permitting window on the one support substrate.

One of the support substrates at the light detection portion of the capillaries can be processed to provide a groove which permits laser beam passage so as to reduce fluorescence reflection from the bottom thereof. The capillaries at the capillary head are cut in an alignment, are inserted closely into corresponding tubes and are secured thereto. One of the methods of securing is to injecting a gluing agent and to cure the same. Through attachment of a cap for protecting the sample injection port, transportation, handling and management of the capillary array can be performed safely. Further, a possible drying of an open end of the capillary array of which use is interrupted can be prevented. The ends of the capillaries at the sample injection port are slightly projected from the metallic tubes.

In the light detection portion, a reflection light shielding film is provided at the opposite side of the window permitting passage of fluorescence. At the sample supply portion for the capillary array a metallic tube electrode is provided which is electrically connected to the electrode for the array head and into which the capillaries are inserted and are secured within the metallic tubes such as by a gluing agent.

The top end of the sample supply portion is adapted so as to permit attachment of a cap for containing buffer solution, thereby, the top end of the sample supply portion is protected during transportation thereof. When interrupting separation and analysis after assembling the capillary array into the electrophoresis apparatus and performing the separation and analysis, buffer solution is introduced into the cap to thereby prevent the top ends of the capillaries from drying, thus a condition permitting reuse of the capillaries at any time can be maintained.

DETAILED DESCRIPTION OF THE PREFERRED EMBODIMENTS

Hereinbelow, embodiments of the present invention will be explained in detail with reference to the drawings.

Figure 1:
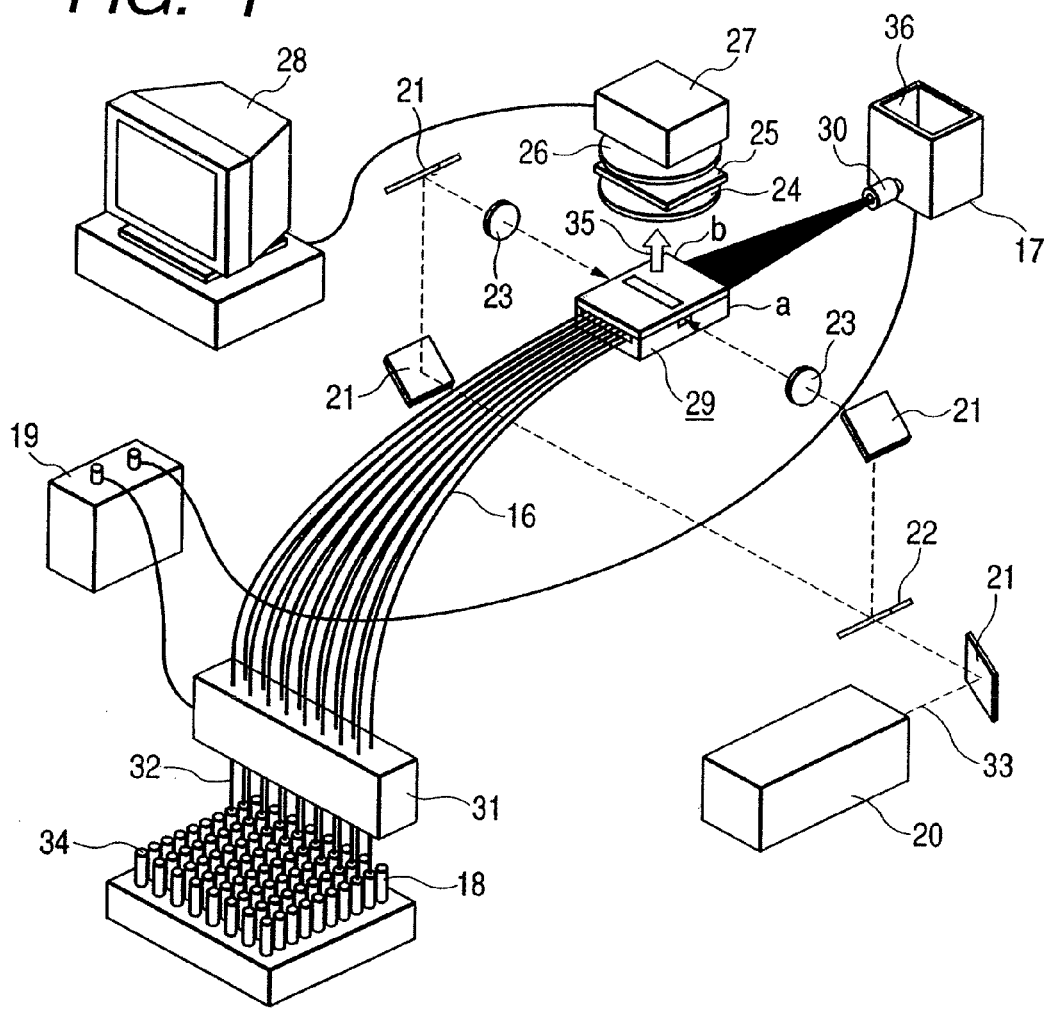
FIG. 1 is a schematic diagram showing an electrophoresis system to which a capillary array of the present invention is applied.
Figure 2:
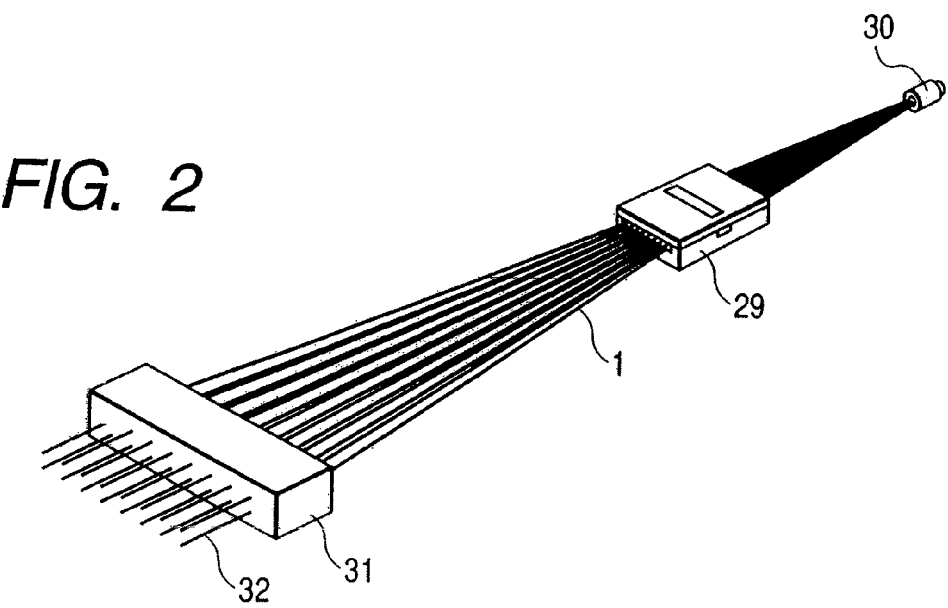
FIG. 2 is a perspective view showing a structure of a capillary array according to the present invention.

FIG. 1 is a schematic diagram when a capillary array of the present invention is applied to an electrophoresis system. A plurality of capillaries, for example, 16 pieces of capillaries, are collected to form an array. At a light detection portion 29 a bottom support plate (glass substrate) "a" and a top support plate (silicon substrate) "b" are provided, and at a window portion thereof a transparent portion of the capillaries which is formed by removing the polyimide coat thereof is provided. FIG. 2 shows an entire structure of the capillary array according to the present invention which includes capillaries 1, the light detection portion 29, a capillary head 30 and a load header 31 with a built-in electrode. The top ends of the capillaries are inserted into electrode tubes 32 and are secured thereto. A voltage for electrophoresis is applied between the capillary head 30 and the load header 31.

In FIG. 1, the laser beam 33 generated from the laser beam source 20 is divided into two parts by the beam splitter 22 and the advancing direction thereof is change by the mirror 21. The laser beam 33 is condensed by a condenser lens 23 and is irradiated to the capillaries 1 from a direction in parallel with the alignment direction of the capillaries 1. The inside of the capillaries 1 is filled with the sample labelled by a fluorescent material (fluorescent sample 34), and when the laser beam 33 is irradiated the fluorescent sample 34 emits fluorescence 35. For the detection of the fluorescence 35, the fluorescence 35 emitted in substantially perpendicular direction with respect to the alignment plane of the capillaries 1 is converted into parallel light by a first lens 24, is effected of image division by an optical filter and image division prism 25, and thereafter image formed on the CCD camera 27 by a second lens 26 and is detected by the CCD camera 27. The detected measurement data is processed by a processing unit 28.

In FIG. 1, the laser beam 33 is irradiated from the both sides of the light detection portion 29, however, the apparatus can be constituted in such a manner that the laser beam 33 is irradiated only from one side thereof. Further, the layout of the light receiving optical system is not limited to that illustrated in FIG. 1. Still further, the number of constituting capillaries 1 is not limited to 16 pieces and the structure of the buffer solution injection port 30 and the conductive fluorescent sample injection port 32 is not also limited to those shown in FIG. 1.

Now, an operation sequence of the capillary array electrophoresis apparatus will be explained. The buffer solution 36 contained in the buffer solution container 17 is injected into the capillaries 1 from the buffer solution injection port 30. Subsequently, the conductive fluorescent sample injection port 32 is immersed in the fluorescent sample container 18 filled with the fluorescent sample 34 and the fluorescent sample 34 is injected into the capillaries 1. Thereafter, the conductive fluorescent sample injection port 32 is immersed in a buffer solution container (not shown) containing a buffer solution, and a high voltage is applied between the buffer solution injection port 30 and the fluorescent sample injection port 32 by the high voltage power source 19 to thereby cause electrophoresis in the capillaries. Since the moving speed by electrophoresis is proportional to the electric charge magnitude of the molecules and is reverse proportional to the mass of the molecules, the fluorescent sample 34 is separated. Through continuous application of the high voltage for a long time the electrophoresis is caused for a long time and the fluorescence 35 emitted at this time is continuously measured.

Figure 3:
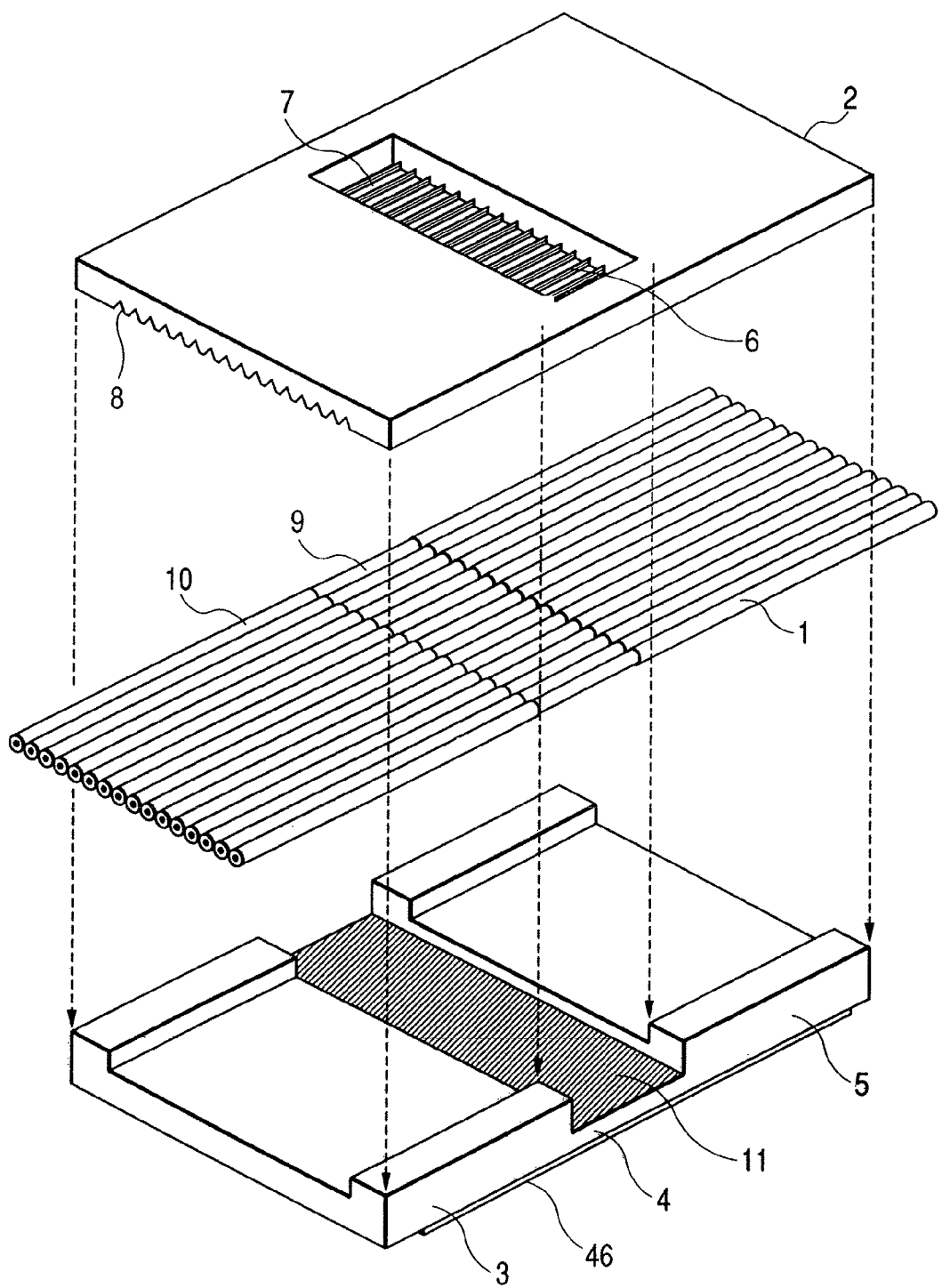
FIG. 3 is an exploded view showing a structure of a light detection portion for a capillary array according to the present invention.

A detailed structure of the light detection portion is shown in FIG. 3. As shown in FIG. 3, between a glass substrate 3 and a silicon substrate 2 the capillaries 1 where a portion 9 being removed of polyimide coat 9 is formed are sandwiched. On the glass substrate 3 a groove 4 is formed which permits passage of laser beam and the bottom of the groove 4 is finished into ground glass. Further, other than the groove portion of the glass substrate 3 forms a laser beam non-irradiation portion 5.

The silicon substrate 2 is provide with a window frames 7 forming windows 6 through which fluorescence is taken out. A black coating 46 is formed outside the glass plate 3 to thereby reduce noises caused by reflection of fluorescence.

Figure 4:
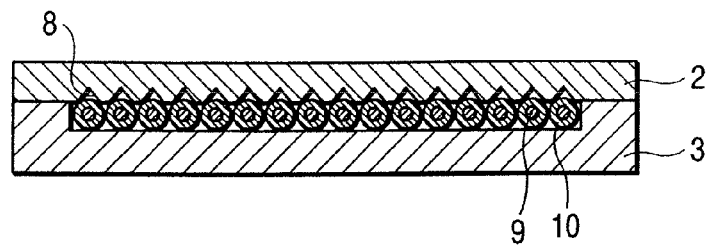
FIG. 4 is a schematic cross sectional view of a structure of a non-irradiation portion in a light detection portion for a capillary array according to the present invention.

FIG. 4 shows a cross sectional view of the laser beam non-irradiation portion 5 in FIG. 3. The surface of the glass substrate 3 where the polyimide coating contacts is processed in such a high accuracy that interference fringes can be observed on the surface and the flatness degree thereof is high. A plurality of capillaries 1 are contacted to the highly flattened surface via the polyimide coating 10 and are aligned thereon. Thereby, the plurality of the capillaries 1 follow the glass substrate 3 and are aligned thereon with high accuracy and easily. V shaped grooves 8 are formed on the silicon substrate 2 and the capillaries 1 are aligned within the grooves 8.

Figure 5A:
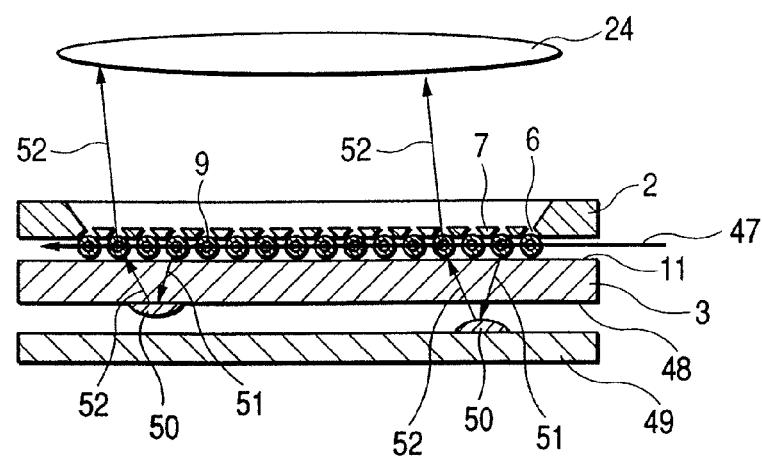
FIGS. 5A and 5B are views for explaining action of black coating in FIG. 3.
Figure 5B:
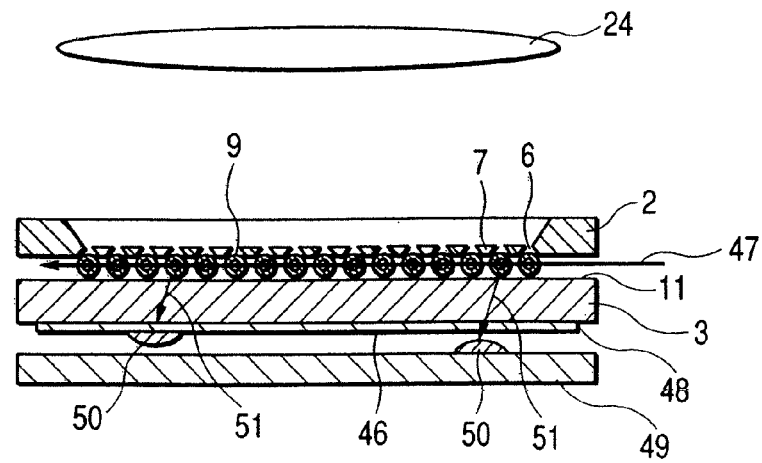

FIGS. 5A and 5B show cross sectional views at the laser beam irradiation portion 4 in FIG. 3, wherein FIG. 5A is a view for explaining when no black coating 46 is formed and FIG. 5B is a view for explaining when the black coating 46 is formed.

When no black coating 46 is provided as shown in FIG. 5A, laser beam 47 penetrates and passes through the plurality of capillaries which are aligned in a high accuracy at this moment, scattered light 51 from the surface of the fused quartz tubes 9 passes through the glass substrate 3 and is irradiated to a fluorescent emitting material on the surface of the opposing member 49 disposed opposite to the glass substrate 3, and the fluorescence 52 emitted thereby returns to the quartz tubes 9, further passes the through window 6 and is directed to the first lens 24 which causes noises. Further, when a fluorescent emitting material 50 deposited on the back face of the glass substrate 3, such likely causes noises.

However, when the black coating 46 is applied on the back face of the glass substrate 3 as shown in FIG. 5B, even if a fluorescent emitting material 50 is contained in the opposing member 49 and further a fluorescent emitting material 50 is deposited after the black coating 46 is applied, the scattered light 51 is absorbed by the black coating 46, thereby, the causes of noises are removed. As a material of the black coating 46 a paint which emits no fluorescence is used. As a typical paint application work a silk screening is used, however, other painting method can be used, and further a manual painting can also be used.

Figure 6:
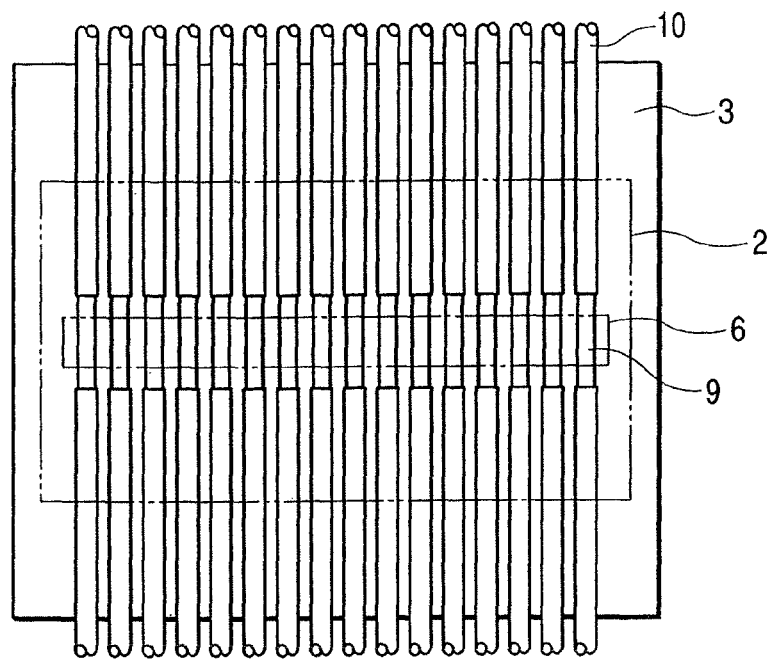
FIG. 6 is a plane view of FIG. 3.

FIG. 6 shows schematically a typical plane view seen from the top in FIG. 3. The silicon substrate 2 is shown by two dots chain lines. The through window 6 provided on the silicon substrate 2 is also shown by two dots chain lines. Further, FIG. 6 shows a state where a plurality of capillaries are aligned for a capillary array.

With FIG. 6 an alignment of the capillaries will be explained. From the portions of the capillaries corresponding to the light detection portion the polyimide resin 10 coating the fused quartz tubes 9 is removed. The removal was conventionally performed, for example, in such a manner that after removing the polyimide coating by a predetermined size one by one separately, then the removed portions are arranged. However, when the polyimide coating is removed one by one by a predetermined removing width, a processing error is caused and the removed width varies. Further, the arrangement is performed in such a manner that the removed portions, in particular, the boundaries (the boundary where the polyimide resin 10 is cut out) align each other, however, such operation likely causes error and takes time. Usually, a non alignment of the boundary portion can be immediately recognized. In the worst case, a remaining polyimide resin can be observed from the through window 6 which causes great adverse effect to the detection.

Therefore, instead of the one by one coating removal, after arranging the plurality of capillaries when the polyimide coating is removed collectively, the removed portions of polyimide resin 10 on the plurality of capillaries are neatly aligned. It is easily recognized which aligning method is used when observing the alignment of the boundaries. The predetermined width and the predetermined position of the polyimide resin removed position can be freely changed inclusively with the plurality of the capillaries.

Figure 7:
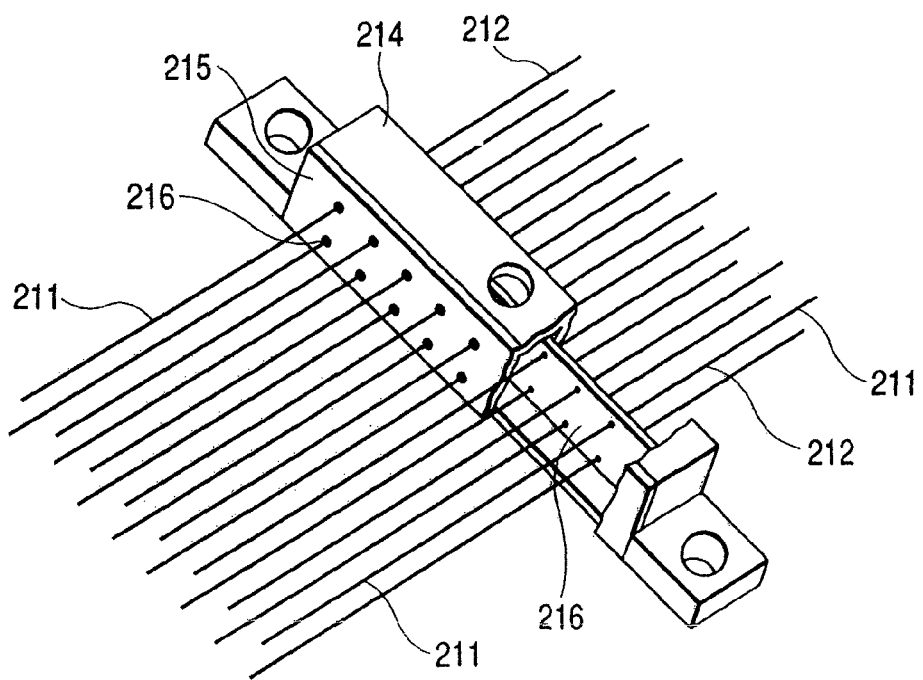
FIG. 7 is a perspective view partly being cut out for explaining a structure of and around a load header used in the present invention.

FIG. 7 is a view for explaining a load header portion representing one embodiment of the present invention. The load header portion is constituted by such as capillaries 211, electrode SUS pipes 212 serving as metallic tubes, a holder 214, a holder cover 215 and an electrode 216. The inside the holder 214 the electrode plate 216 of phosphor bronze through which the SUS pipes 212 are passed and welded thereto is assembled. As shown in FIG. 7, the capillaries 211 pass through respective holes in the holder cover 215 and the SUS pipes 212 and project at the opposite end face of the SUS pipes 212 by less than 1 mm.

The top ends of 16 pieces of capillaries at the side of the load header into which the capillary head is assembled are cut and aligned to a length of L+10 mm from the center of the fluorescent detection portion. Wherein L is the length of a capillary from the center of the fluorescent detection portion to the top end of the load header after completing assembly of the header, and is required depending on separation performance of a sequencer and electrophoresis time to have a predetermined length as, for example, being designed in the length of 220 mm, 360 mm, 500 mm and 800 mm. Subsequently, the capillaries 211 are inserted through the holes of the load header cover 215 into the corresponding SUS pipes 212. After adjusting the respective capillaries 211 so as to project from the top ends of the SUS pipes 212 by 10 mm, a gluing agent is injected into the holes of the load header 215 to thereby secure the respective capillaries to the load header cover 215.

Figure 8:
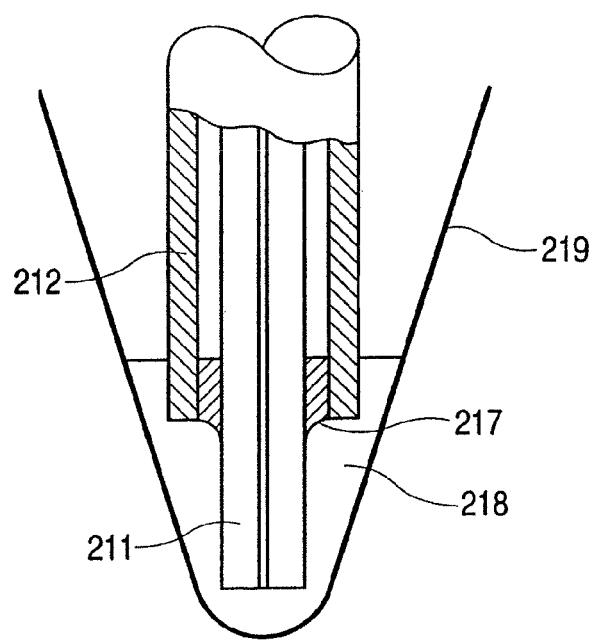
FIG. 8 is a cross sectional view for explaining a specific structure of top ends of capillaries used in the present invention.

Now, a processing of the top end portion of the load header will be explained. FIG. 8 is an enlarged cross sectional view for explaining the same. As shown in the drawing, a gluing agent 217 is injected between the SUS pipe 212 and the capillary 211 to seal the gap therebetween. Thereafter, with a cutting device using a blade the top end of the capillary 211 is cut to a projecting length of 0.5~1.0 mm from the end face of the SUS pipe 212. With these operations, the length of the respective capillaries from the top end of the load header to the fluorescent detection portion can be aligned to a predetermined length, thereby, the electrophoresis time for the 16 pieces of the capillaries can be uniformalized. Further, the sealing structure of the gap between the SUS pipes 212 and the capillaries 211 is an indispensable measure to prevent the sample solution from penetrating into the gap as well as to prevent a possible carry-over when performing measurement on other samples.

Now, the length of the capillaries 211 from the top ends of the SUS pipes 212 is required more than 0.5 mm so as to form an optimum electric field for introducing DNA molecules into the capillaries. On the other hand, as shown in FIG. 8, when measuring a micro amount of sample in a degree of micro litter, it is necessary to limit the top end length of the capillaries 211 below 1.0 mm. Therefore, the length of 0.5~1.0 mm is a proper length both for the gluing agent injection work to the top end of the SUS pipes and the cutting work of top ends of the capillaries.

Another top end configuration of the SUS pipe 212 for the load header representing another embodiment of the present invention will be explained. Although the entire outlook structure thereof is substantially the same as the above embodiment, a SUS pipe 212 having a conically spread shape at a top end at the side being incorporated inside the holder is used. As a result, when inserting capillaries 211 from the holes in the load header cover 215 into the SUS pipes 212, the capillaries 211 can be easily inserted even if the centers of the both are slightly offset which produces an advantage of enhancing workability.

Figure 9:
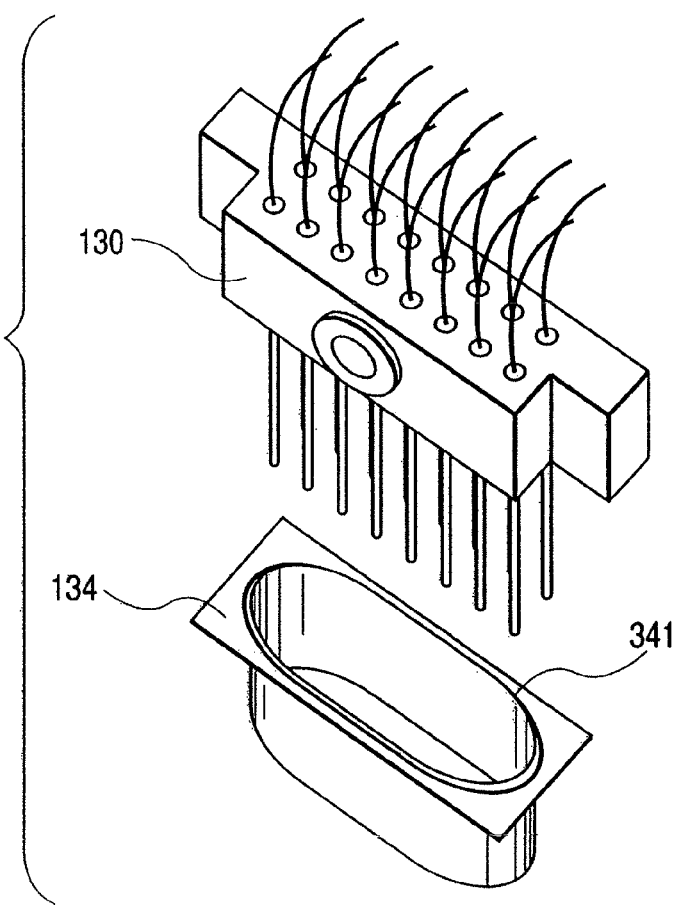
FIG. 9 is a perspective view for explaining a relationship between the load header and a protective cap used in the present invention.

FIG. 9 is a perspective view showing a relationship between the sample injection portion of the capillary array and a protective cap therefor in the present invention. The sample injection portion at the top end of the load header 130 for the capillary array is designed to permit fitting into a cap 341. Thereby, the capillary array is protected during transportation thereof, moreover, when temporarily interrupting an operation of an electrophoresis apparatus using such capillary array or when storing the capillary array after removing the same from the electrophoresis apparatus for some reason, if a buffer solution is introduced into the cap 341 and the capillary array is immersed in the buffer solution, the capillary array can be protected. A flange portion 134 for the cap 341 is provided for achieving close contact with the load header 130.

Figure 10:
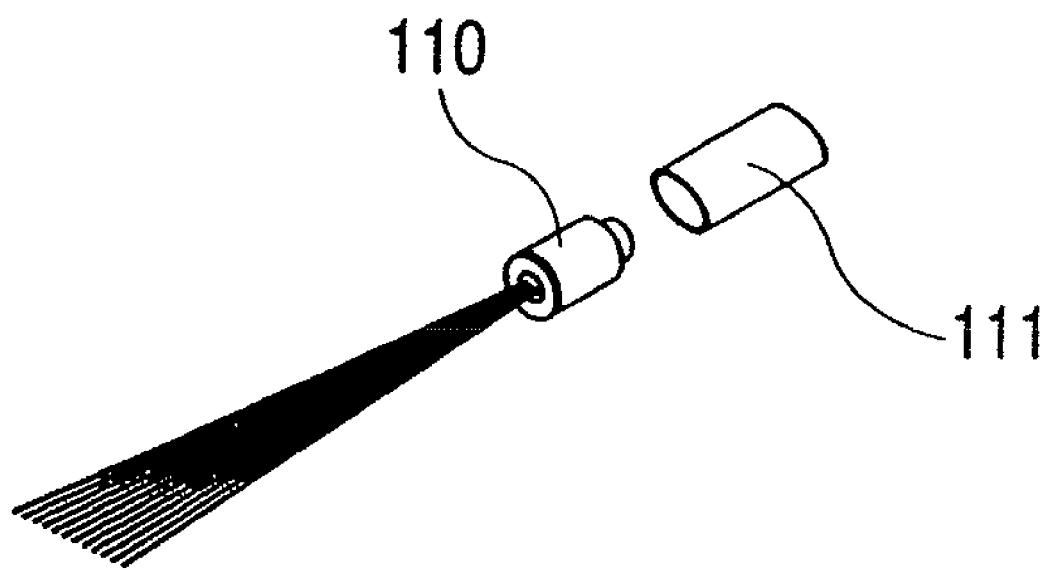
FIG. 10 is a perspective view showing a structure of a capillary head portion according to the present invention.

FIG. 10 is a diagram showing a relationship between the capillary head and the protective cap therefor in the present invention. The capillary head 110 is designed to permit fitting into a cap 111 of silicon rubber. Thereby, like the protective cap 341, the capillary array can be protected during transportation thereof. Further, when storing the capillary array after removing the same from the electrophoresis apparatus, a possible drying of the top end of the capillary head can be prevented.

Each of the capillaries 1 used in the capillary array as explained above is a fused quartz tube having inner diameter of 50±10 μm and outer diameter of 340±20 μm. Since the fused quartz tube itself breaks very easily, a polyimide coating having thickness of 15±5 μm is applied on the surface of the capillary. In view of limiting amount of fluorescent sample 34 it is desirable to reduce the inner diameter of the capillary, however, on the other hand in view of a concave lens effect due to refractive index difference between the fluorescent sample 34 and fused quartz, the capillary having a too small inner diameter makes the measurement difficult. Therefore, the inner diameter of 50~100 μm is preferable for the quartz tube. Further, in order to suppress the above refractive index difference it is preferable that the outer diameter of the fused quartz tube is small, however, a too small outer diameter makes assembling thereof difficult because of static electricity, therefore, the outer diameter of 250~350 μm is preferable for the fused quartz tube. The coating material for the capillary 1 is not limited to the polyimide, a material having an equivalent electrical insulation and other properties as those of polyimide can be used.

As has been explained above, the capillary array of the present invention is provided with basic functions necessary for electrophoresis and includes in integration the light detection portion, the voltage application portion and the buffer solution gel supply portion which are necessary for incorporating into the electrophoresis apparatus.

According to the present invention, a capillary array can be provided which is easy to handle, ensures a sufficient mechanical protection and facilities attachment and detachment to a concerned electrophoresis apparatus.

The invention claimed is:

1. A set comprising a capillary array and a cap that is permitted to attach said cap to said capillary array when said capillary array is removed from an electrophoresis apparatus and is stored,
    wherein said capillary array is removably attached to the electrophoresis apparatus and includes a plurality of capillaries, each being provided with a sample injection port and an electrophoresis medium injection port, a holder portion that spreads the sample injection ports of the plurality of capillaries from one another and holds the same, a light detection portion in which a portion of the plurality of capillaries are aligned to which excitation light is irradiated, and said cap includes a container portion that contains buffer solution and a close contact making portion that closely contacts the holder portion,
    wherein said cap is structured to be able to accommodate the sample injection ports of the capillaries therein when the close contact making portion is closely contacted to the holder portion, and
    wherein the close contact making portion is a flange portion extending outward from the upper portion of the container portion.

2. The set of claim 1, further comprising another cap that is configured to be fitted to a capillary head formed by bundling the electrophoresis medium ports.

\* \* \* \* \*